United States Patent [19]

Gaffar et al.

[11] Patent Number: 4,889,712

[45] Date of Patent: * Dec. 26, 1989

[54] ANTICALCULUS ORAL COMPOSITION

[75] Inventors: Abdul Gaffar, Princeton; Shek-Hong H. Lau, Dayton; John Afflito, Brookside; Arline M. Nykvist, Bloomsbury, all of N.J.

[73] Assignee: Colgate-Palmolive Company, Piscataway, N.J.

[*] Notice: The portion of the term of this patent subsequent to Dec. 9, 2003 has been disclaimed.

[21] Appl. No.: 169,915

[22] Filed: Mar. 18, 1988

[51] Int. Cl.⁴ .................... A61K 7/16; A61K 7/18
[52] U.S. Cl. .................... 424/52; 424/49; 424/57
[58] Field of Search ............ 424/49, 52, 57, 83

[56] References Cited

U.S. PATENT DOCUMENTS

| Number | Date | Inventor | Class |
|---|---|---|---|
| 3,429,963 | 2/1969 | Shedlovsky | 424/56 |
| 3,927,201 | 12/1975 | Baines et al. | 424/54 |
| 3,927,202 | 12/1975 | Harvey et al. | 424/57 |
| 3,956,480 | 5/1976 | Dichter et al. | 424/54 |
| 3,976,765 | 8/1976 | Nachtigal | 424/54 |
| 4,138,477 | 2/1979 | Gaffar | 424/52 |
| 4,183,914 | 1/1980 | Gaffar et al. | 424/48 |
| 4,217,342 | 8/1980 | Gaffer et al. | 424/48 |
| 4,217,343 | 8/1980 | Gaffar et al. | 424/48 |
| 4,340,583 | 7/1982 | Wason | 424/52 |
| 4,515,772 | 5/1985 | Parran et al. | 424/57 |
| 4,590,066 | 5/1986 | Parran et al. | 424/52 |
| 4,627,977 | 12/1986 | Gaffar et al. | 424/52 |
| 4,661,341 | 4/1987 | Benedict et al. | 424/48 |
| 4,684,518 | 8/1987 | Parran et al. | 424/52 |

*Primary Examiner*—Shep K. Rose
*Attorney, Agent, or Firm*—Murray M. Grill; Robert L. Stone

[57] ABSTRACT

In an anticalculus oral composition containing in an orally acceptable vehicle one or a mixture of water soluble linear molecularly dehydrated alkali metal or ammonium polyphosphate salts as essential anticalculus agent, an amount of a fluoride ion source sufficient to supply about 25 ppm to about 2,000 ppm of fluoride ions, and one or a mixture of water soluble alkali metal or ammonium synthetic anionic polymeric polycarboxylate salts, the improvement comprising employing in said composition a polyphosphate ion:polycarboxylate salt weight ratio ranging from about 0.3:1 to about 2.5:1.

19 Claims, No Drawings

ANTICALCULUS ORAL COMPOSITION

This application is a continuation-in-part of application Ser. No. 842,101, filed Mar. 20, 1986, now U.S. Pat. No. 4,806,340 which is in turn a continuation-in-part of application Ser. No. 775,851, now U.S. Pat. No. 4,627,977.

This invention relates to oral compositions containing an anticalculus agent.

Calculus is a hard, mineralized formation which forms on the teeth. Regular brushing aids in preventing a rapid build-up of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline HAP is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including HAP. It is apparent therefore that agents which effectively interfere with crystalline growth of HAP will be effective as anticalculus agents. A suggested mechanism by which the anticalculus agents of this invention inhibit calculus formation probably involves an increase of the activation energy barrier thus inhibiting the transformation of precursor amorphous calcium phosphate to HAP.

Studies have shown that there is a good correlation between the ability of a compound to prevent HAP crystalline growth in vitro and its ability to prevent calcification in vivo, provided of course that such compound is stable in an inert to saliva and its components.

It is well known in the art that water soluble hexametaphosphates, tripolyphosphates and pyrophosphates and the like are effective calcium and magnesium ion suppressors, inhibitors, sequestrants and/or chelating agents, and are effective inhibitors of HAP formation in vitro. U.S. Pat. No. 4,515,772 issued May 7, 1985 to Parran et al discloses and claims oral anticalculus compositions containing a fluoride ion source and soluble dialkali metal pyrophosphates alone or admixed with tetraalkali metal pyrophosphates. The voluminous number of acknowledged prior art and "References Cited" in this patent indicate the many uses and functions of these polyphosphates hitherto proposed in oral compositions.

However, as in part admitted in the aforesaid patent disclosure and as shown in the above-mentioned parent patent applications, these linear molecularly dehydrated polyphosphates (i.e. hexametaphosphate, tripolyphosphates, pyrophosphates, etc.) in common, when introduced into the oral cavity and/or saliva are significantly hydrolyzed by salivary enzymes (phosphatases) to orthophosphates which are ineffective as inhibitors of HAP formation.

The aforesaid U.S. Pat. No. 4,627,977, the disclosure of which is incorporated herein, discloses oral compositions containing polyphosphate as anticalculus agent and a combination of fluoride and polymeric polycarboxylate to inhibit the enzymatic hydrolysis of the polyphosphate in saliva. The aforesaid application Ser. No. 842,101, the disclosure of which is also incorporated herein, discloses dentifrices of similar composition containing as polyphosphate at least about 4.3% tetrapotassium pyrophosphate and up to about 2.7% tetrasodium pyrophosphate, thus eliminating the problem of grittiness when incorporating more than about 2.7-3% of the relatively insoluble tetrasodium salt.

Problems still exist concerning these compositions in the form of objectionable taste tendencies of the tetrapotassium salts and the tendency towards decreased anticaries effects of the fluoride with increasing amounts of polyphosphate ion.

It is an object of this invention to provide an improved anticalculus oral composition which will not be subject to one or more of the above problems and disadvantages.

A further object of this invention is the provision of such a composition containing relatively lower proportions of polyphosphate ion, especially pyrophosphate ion, and/or lower to zero proportions of potassium polyphosphates, especially tetrapotassium pyrophosphate.

A still further object of the invention is to provide an oral composition which inhibits the transformation of amorphous calcium phosphate to HAP crystal structure normally associated with calculus and is effective over a relatively wide pH range and/or with improved cosmetic properties.

Another object of this invention is the provision of an improved method for inhibiting the formation of calculus.

Other objects and advantages will appear as the description proceeds.

In accordance with certain of its aspects, the invention relates to an oral composition containing in an orally acceptable vehicle, approximately by weight, an effective anticalculus amount in the range of 0.1 to 7%, preferably to below 3%, more preferably to 1.3%, still more preferably 0.5 to 1.3%, of one or a mixture of water soluble linear molecularly dehydrated alkali metal or ammonium polyphosphate, especially pyrophosphate, salts as essential anticalculus agent, an amount of a fluoride ion source sufficient to supply 25 ppm to 2,000 ppm of fluoride ions, and one or a mixture of water soluble alkali metal or ammonium synthetic anionic polymeric polycarboxylate salts having a molecular weight of about 1,000 to about 1,000,000, the polyphosphate ion:polycarboxylate salt weight ratio ranging from about 0.3:1 to about 2.5:1, preferably about 0.5:1 to about 2:1, more preferably about 0.8:1 to about 1.2:1.

It has been found that use of the aforementioned polyphosphate ion:polycarboxylate salt ratios, especially pyrophosphate ion:polycarboxylate salt ratios, unexpectedly enables the attainment of the above-mentioned objects of this invention. Concentrations of polyphosphate ion, especially pyrophosphate ion, may be thereby lowered to below about 3 wt.%, even below about 1.5 wt.%, e.g. in a range of about 0.1 to about 1.3 wt.%, preferably about 0.5 to about 1.3 wt.%. The sodium polyphosphate salts, especially tetrasodium pyrophosphate, may be employed within these ranges without giving rise to the problem of grittiness or the need for the alternative of employing the more soluble potassium salts, which are more expensive and tend to introduce taste problems, especially tetrapotassium pyrophosphate. Anticalculus results of use of composition containing the aforementioned polyphosphate ion:-polycarboxylate salt ratios are unexpectedly usually as good as and often better than compositions containing other ratios.

Synthetic anionic polymeric polycarboxylates and their complexes with various cationic germicides, zinc and magnesium have been previously disclosed as anticalculus agents per se in, for example U.S. Pat. No. 3,429,963 to Shedlovsky and instant assignee, U.S. Pat. No. 4,152,420 to Gaffar and instant assignee, U.S. Pat. No. 3,956,480 to Dichter et al. and instant assignee, U.S. Pat. No. 4,138,477 to Gaffar and instant assignee, and U.S. Pat. No. 4,183,914 to Gaffar et al. It is to be understood that the synthetic anionic polymeric polycarboxylates so disclosed in these patents are operative in the compositions and methods of this invention and such disclosures are to that extent incorporated herein by reference thereto.

The synthetic anionic polymeric polycarboxylates employed herein are, as indicated above, well known, being often employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene), having a molecular weight (M.W.) of about 30,000 to about 1,000,000, preferably to about 500,000, more preferably to about 250,000. These copolymers are available for example as Gantrez AN 139 (M.W. 500,000), A.N. 119 (M.W. 250,000) and preferably S-97 Pharmaceutically (M.W. 70,000), of GAF Corporation. The term "synthetic" is intended to exclude known thickening or gelling agents comprising carboxymethylcellulose and other derivatives of cellulose and natural gums.

Other operative polymeric polycarboxylates include those disclosed in U.S. Pat. No. 3,956,180 referred to above such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000, and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred U.S. Pat. No. 4,138,477 and 4,183,914 include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acid containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alphaphenylacrylic, 2-benzyl acrylic, 2-cyclohexylacrylic, angelic, umbellic, fumaric, maleic acids and anhydrides. Other different olefinic monomers copolymerizable with such carboxylic monomers include vinyl acetate, vinyl chloride, dimethyl maleate and the like. Copolymers contain sufficient carboxylic salt groups for water-solubility.

Also useful herein are so-called carboxyvinyl polymers, disclosed as toothpaste components in U.S. Pat. No. 3,980,767 issued Sept. 14, 1976 to Choun et al, U.S. Pat. No. 3,935,306 issued Jan. 27, 1976 to Roberts et al, U.S. Pat. No. 3,919,409 issued Nov. 11, 1975 to Perla et al, U.S. Pat. No. 3,911,904 issued Oct. 7, 1975 to Harrison, and U.S. Pat. No. 3,711,604 issued Jan. 16, 1973 to Colodney et al. They are commercially available for example under the trademarks Carbopol 934, 940 and 941 of B. F. Goodrich, these products consisting essentially of a colloidally water-soluble polymer of polyacrylic acid crosslinked with from about 0.75% to about 2.0% of polyallyl sucrose or polyallyl pentaerythritol as cross-linking agent.

The synthetic anionic polymeric polycarboxylate component is mainly a hydrocarbon with optional halogen and O-containing substituents and linkages as present in for example ester, ether and OH groups, and when present is generally employed in the instant composition in approximate weight amounts of 0.05 to 5%, preferably 0.05 to 4%, more preferably 0.1 to 3%. Amounts in the upper portions of these ranges are typically employed in dentifrice compositions containing a dental abrasive and used in conjunction wih brushing of the teeth, e.g. tooth pastes (including creams), gels, powders and tablets. Amounts in excess of these ranges may be employed for thickening or gelling purposes.

The sources of fluoride ion, or fluoride-providing compounds, required according to this invention as an essential acid phosphatase and pyrophosphatase enzyme inhibitor component, are well known in the art as anticaries agents and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorozirconate, sodium monofluorophosphate, aluminum mono- or di-fluorophosphate, and fluorinated sodium calcium pyrophosphate. Alkali metal and tin fluorides such as sodium and stannous fluorides sodium monofluorophosphate (MFP) and mixtures thereof, are preferred.

The amount of fluoride-providing compound is dependent to some extent upon the type of compound, its solubility, and the type of oral preparation, but it must be a nontoxic amount, generally about 0.005 to about 3.0% in the preparation. In a dentifrice preparation, e.g. dental gel, toothpaste (including cream), toothpowder, or dental tablet, an amount of such compound which releases up to about 5,000 ppm of F ion by weight of the preparation is considered satisfactory. Any suitable minimum amount of such compound may be used, but it is preferable to employ sufficient compound to release abut 300 to 2,000 ppm, more preferably about 800 to about 1,500 ppm of fluoride ion. Typically, in the cases of alkali metal fluorides and stannous fluoride, this compound is present in an amount up to about 2% by weight, based on the weight of the preparation, and preferably in the range of about 0.05% to 1%. In the case of sodium monofluorophosphate, the compound may be present in an amount of about 0.1-3%, more typically about 0.76%.

In oral preparations such as mouthwash, lozenges and chewing gum, the fluoride-providing compound is typically present in an amount sufficient to release up to about 500 ppm, preferably about 25 to about 300 ppm by weight of fluoride ion. Generally about 0.005 to about 1.0 wt.% of such compound is present.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The pH of such liquid and other preparations of the invention is generally in the range of from about 4.5 to about 10 and typically from about 5.5 to 9. The pH is preferably in the range of from about 6 to about 8.0. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain other desirable forms of this invention, the oral composition may be substantially solid or pasty in character, such as toothpowder, a dental tablet, a toothpaste, gel or dental cream. The vehicle of such solid or pasty oral preparations generally contains polishing material. Examples of polishing materials are water-insoluble sodium metaphosphate, potassium metaphosphate tricalcium phosphate, dihydrated calcium phosphate, anhydrous dicalcium phosphate, calcium pyrophosphate, magnesium, orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 3,070,510 of Dec. 15, 1962 such as melamine-, phenolic-, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 cm.$^2$/gm., silica gel or colloidal silica, and complex amorphous alkali metal aluminosilicate.

When visually clear gels are employed, a polishing agent of colloidal silica, such as those sold under the trademark SANTOCEL as Santocel 100 and alkali metal alumino-silicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also included small amounts of soluble material. Thus, insoluble sodium metaphosphate may be formed in any suitable manner as illustrated by Thorpe's *Dictionary of Applied Chemistry*, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, should be reduced or eliminated as by washing with water. The insoluble alkali metal metaphosphate is typically employed in powder form of a particle size such that no more than about 1% of the material is larger than about 37 microns.

The polishing material is generally present in the solid or pasty compositions in weight concentrations of about 10% to about 99%. Preferably, it is present in amounts ranging from about 10% to about 75% in toothpaste, and from about 70% to about 99% in toothpowder.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol (e.g. 400-600) exemplify suitable humectants/carriers. Also advantageous are liquid mixtures of water, glycerine and sorbitol. In clear gels where the refractive index is an important consideration, about 3-30 wt.% of water, 0 to about 80 wt.% of glycerine, and about 20-80 wt.% of sorbitol is preferably employed.

Toothpastes, creams and gels typically contain a natural or synthetic thickener or gelling agent in proportions of about 0.1 to about 10, preferably about 0.5 to about 5, wt.%. A suitable thickener is synthetic hectorite, a synthetic colloidal magnesium alkali metal silicate complex clay available for example as Laponite (e.g. CP, P 2002, D) marketed by Laporte Industries Limited. Laponite D analysis shows, approximately by weight, 58.00% $SiO_2$, 25.40% $MgO$, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are watersoluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compound reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (.e.g sorbitan monostearate) and polypropyleneoxide (e.g. Pluronic materials).

Various other materials may be incorporated in the oral preparations of this invention such as whitening agents, preservatives, silicones, chlorophyll compounds, other anticalculus agents, and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, APM (aspartyl phenylalanine methyl ester), saccharine and the like. Suitably, flavor and sweetening agents may together comprise from about 0.1% to 5% more of the preparation.

In the preferred practice of this invention an oral composition according to this invention such as a mouthwash or dentifrice is applied regularly to the oral cavity as by "swishing" or brushing dental surfaces, such as every second or third day or preferably from 1 to 3 times daily, at a pH of about 4.5 to about 10, generally about 5.5 to about 9, preferably about 6 to 8, for at least 2 weeks up to 8 weeks or more up to lifetime. The composition is typically removed by rinsing with water after each application.

The compositions of this invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The vehicle or carrier in a tablet or lozenge is a noncariogenic solid water soluble soluble polyhydric alcohol (polyol) such as mannitol, xylitol, sorbitol, maltitol, a hydrogenated starch hydrolysate, Lycasin, hydrogenated glucose, hydrogenated disaccharides, and hydrogenated polysaccharides, in an amount of about 90-98% by weight of the total composition. Solid salt such as sodium bicarbonate, sodium chloride, potassium bicarbonate or potassum chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and carbowax.

Lozenge formulations contain about 2% gum as barrier agent to provide a shiny surface as opposed to a tablet which has a smooth finish. Suitable non-cariogenic gums include Kappa carrageenan, carboxymethyl cellulose, hydroxyethyl cellulose, Gantrez, and the like.

The lozenge or tablet may optionally be coated with a coating material such as waxes, shellac, carboxymethyl cellulose, polyethylene/maleic anhydride copolymer or Kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following examples are further illustrative of the nature of the present invention, but it is understood that the invention is not limited thereto. All amounts and proportions referred to herein and in the appended claims are by weight and temperatures are in degrees C. unless otherwise indicated.

EXAMPLE 1

IN VITRO INHIBITION OF HAP FORMATION

The in vitro formation of HAP is measured titrimetrically via a pH stat procedure. Stock solutions of 0.1M $CaCl_2$ and 0.1M $NaH_2PO_4$ are prepared fresh in $CO_2$-free deionized distilled water. To 23 ml. $CO_2$-free deionized distilled water 1.0 ml. of the stock phosphate solution and independently 1.0 ml. of aqueous solutions containing concentrations of components listed in Table 1 below of the anticalculus composition being tested are added followed by 1.0 ml. of the stock calcium chloride solution which initiates the reaction. The reaction is conducted at 25° C. and pH 7.4 under a nitrogen atmosphere. Consumption of 0.1N NaOH is recorded automatically from which the time required for crystal formation is determined. TABLE 1 shows the results of this procedure.

TABLE 1

| Pyrophosphate[1] Anion (ppm) | Gantrez[2] (ppm.) | Pyro/Gantrez Wt./Ratio | NaF (ppm) | Time(min.) of HAP Crystal Formation |
|---|---|---|---|---|
| 0 (water control) | 0 | — | — | 19 |
| 0 | 20 | — | — | 20 |
| 10 | 0 | — | — | 31.5 |
| 10 | 5 | 2:1 | — | 32 |
| 10 | 10 | 1:1 | — | 32.5 |
| 10 | 20 | 0.5:1 | — | 40 |
| 20 | 0 | — | — | 33.0 |
| 20 | 5 | 4:1 | — | 37.5 |
| 20 | 10 | 2:1 | — | 59.5 |
| 20 | 20 | 1:1 | — | 65.9 |
| 20 | 22 | 0.9:1 | — | 66.0 |
| 20 | 20 | 1:1 | 1.7 | 66.0 |
| 20 | 40 | 0.5:1 | — | 50.2 |
| 20 | 40 | 0.5:1 | 1.7 | 51.5 |

TABLE 1 shows that at the threshold level of 20 ppm, the delay in HAP formation is 14.0 minutes (33-19) with pyrophosphate anion alone, and with Gantrez alone is essentially non-existent (20-19). However, the combination of 20 ppm pyrophosphate anion and 20 ppm Gantrez unexpectedly yields a prolonged delay of about 47 minutes (65.9-19), indicating synergism.

The validity of the use of the 20 ppm level is based on the separation of chelation vs. crystal growth inhibition. In the above test, the crystal growth inhibition occurs at a substoichiometric ratio (calcium in the system is 160 ppm vs. the 20 ppm pyro, a ratio of 8:1 indicating it is not merely a chelation effect).

As shown in the following TABLE A based on previous studies, 18.8 mg. of pyrophosphate anion is retained in the mouth from 2% tetrasodium pyrophosphate (1.3% pyrophosphate anion) which is equivalent to 18,000 ppm of pyro.

TABLE A

PYROPHOSPHATE ION ORAL RETENTION STUDIES (SOLUTION)

| Original Tetrasodium Pyrophosphate in solution (%) | Amount of Pyrophosphate delivered (mg) | Amount of Pyrophosphate retained (mg) | Average Pyrophosphate retained (mg) |
|---|---|---|---|
| 3.3 | 499.5 | 62.4 | 60.5 |
| 3.3 | 504.0 | 58.6 | |
| 2.0 | 293.6 | 17.0 | 18.8 |
| 2.0 | 297.5 | 20.6 | |
| 0.5 | 76.7 | 19.9 | 20.2 |
| 0.5 | 76.1 | 20.5 | |

Humans normally secrete about 1 to 1.5 liters of saliva per day. Therefore the equivalent concentration is 18,800/1,000 or 18.8 ppm per unit time in the mouth. This is the rationale for the 20 ppm level for determining the continuous threshold effect for HAP inhibition.

EXAMPLE 2

IN VIVO CALCULUS INHIBITION

Twenty-one day old male weanling Sprague-Dawley rats were randomized into 12 animals per group. The animals were fed a calculogenic diet (RC-16') and deionized water, ad libitum. At the beginning of the study, all animal were inoculated with a suspension of S. mutans (67615) and A. viscosus (OMZ-105-N14) to stimulate plaque and calculus formation.

Each rat was treated once daily (except Saturday and Sunday) with 0.2 ml. of test solution delivered intraorally with an automatic pipettor. All animals were sacrificed after three weeks of treatment and the jaws were stripped of flesh and prepared for calculus scoring.

Calculus on both maxillary and mandibular quadrants was evaluated using the calculus surface severity index method of Briner and Francis[1]. The results of the study are listed in TABLE 2. The "Gantrez" in the test solutions was S97, as in EXAMPLE 1. The pyrophosphate ion ("Pyro") in the test solutions was derived from a 3:1 mixture of tetrapotassium pyrophosphate:tetrasodium pyrophosphate. "SD" means Standard Deviation. Mean Calculus/Rat is based on 12 rats per group. Significance at 95% level.

TABLE 2

| Test Solution | Pyro: Gantrez | Mean Calculus/ Rat | ∓SD | % Reduction from Water |
|---|---|---|---|---|
| Water Control | — | 78.25 | 19.78 | — |
| 3.3% Pyro, 1.0% Gantrez, 0.24% NaF (Positive Control) | 3.3:1 | 48.66 | 16.68 | −37.81 |
| 2.3% Pyro, 1.5% Gantrez, 0.24% NaF | 1.5:1 | 53.91 | 22.71 | −31.10 |
| 1.5% Pyro, 1.5% Gantrez, 0.24% NaF pH 7.0 | 1:1 | 55.33 | 17.41 | −29.29 |

1. Briner, M.W. and Francis, M.D. "In vitro and in vivo evaluation of anti-calculus agents." Calcified Tissue Research 11:10-22 (1973).

TABLE 2 shows that compared to the placebo (water control), all test solutions containing pyrophosphate ion, Gantrez copolymer and sodium fluoride significantly reduced the incidence of calculus, and all tested pyro:Gantrez ratio produced substantially equal and acceptable anticalculus results.

The following examples illustrate preferred compositions embodying the teachings of this invention.

EXAMPLE 3

DENTIFRICE COMPOSITION

| Ingredient | Parts |
|---|---|
| Sorbitol (70% solution) | 30.000 |
| Deionized water | 25.047 |
| Zeodent 113 (silicon dioxide) | 20.000 |
| Glycerine | 10.000 |
| PEG 600 (polyethylene glycol) | 3.000 |
| Sylox 15 (synthetic silica) | 3.000 |
| Tetrasodium pyrophosphate (TSPP) | 2.000* |
| Gantrez (S-97 Pharmaceutical grade) | 1.500 |
| Sodium lauryl sulfate | 1.200 |
| Sodium hydroxide (50% solution) | 1.000 |
| Flavor | 0.950 |
| Iota carrageenan | 0.750 |
| Titanium dioxide | 0.500 |
| Sodium saccharin | 0.300 |
| Sodium fluoride | 0.243 |

*provides 1.3 parts pyrophosphate ion.

EXAMPLE 4

MOUTHWASH

|  | Parts |
|---|---|
| TSPP | 1.6* |
| Ethyl Alcohol | 15.0 |
| Gantrez S-97 | 1.0 |
| Glycerol | 10.0 |
| Flavor | 0.4 |
| Sodium Saccharin | 0.03 |
| NaF | 0.05 |
| Pluronic F 108** | 2.0 |
| Deionized Water to Q.S. | 100 |

*provides 1.04 parts pyrophosphate ion
**Polyoxyethylenated polyoxypropylene nonionic block polymer surfactant

EXAMPLE 5

LOZENGES

|  | PARTS |
|---|---|
| Sugar | 75–98 |
| Corn syrup | 1–20 |
| Flavor oil | 0.1–1.0 |
| Tablet lubricant | 0.1–5 |
| TSPP | 0.1–5 |
| Gantrez S-97 | 0.3–17 |
| NaF | 0.005–0.1 |
| Water | 0.01–0.2 |

EXAMPLE 6

CHEWING GUM

|  | Parts |
|---|---|
| Gum base | 10 to 50 |
| Binder | 3 to 10 |
| Filler (sorbitol, mannitol or combination thereof) | 5 to 80 |
| Artificial sweetener | 0.1 to 5 |
| TSPP | 0.1 to 5 |
| Gantrez S-97 | 0.3 to 17 |
| NaF | 0.005–0.1 |
| Flavor | 0.1 to 5 |

This invention has been described with respect to certain preferred embodiments and it will be understood that modifications and variations thereof obvious to those skilled in the art are to be included within the purview of this application and the scope of the appended claims.

We claim:

1. In an anticalculus oral composition containing in an orally acceptable vehicle one or a mixture of water soluble linear molecularly dehydrated alkali metal or ammonium polyphosphate salts as essential anticalculus agent, an amount of a fluoride ion source sufficient to supply about 25 ppm to about 2,000 ppm of fluoride ions, and one or a mixture of water soluble alkali metal or ammonium synthetic anionic polymeric polycarboxylate salts, the improvement comprising employing in said composition a polyphosphate ion:polycarboxylate salt weight ratio ranging from about 0.3:1 to about 2.5:1.

2. A composition according to claim 1 wherein said fluoride ion source comprises sodium fluoride.

3. A composition according to any one of claims 1 or 2 wherein said polymeric polycarboxylate has a molecular weight of about 1,000 to about 1,000,000.

4. A composition according to any one of claims 1, 2 or 3 wherein said polymeric polycarboxylate comprises a carboxyvinyl polymer.

5. A composition according to any one of claims 1, 2 or 3 wherein said polymeric polycarboxylate comprises a copolymer of vinyl methyl ether and maleic acid or anhydride.

6. A composition according to claim 5 wherein said copolymer has a molecular weight of about 30,000 to 500,000.

7. A composition according to claim 5 wherein said copolymer has a molecular weight of about 70,000.

8. A composition accordng to any one of claims 1 to 7 containing about 0.1 to about 7 wt. percent of said polyphosphate salt or mixture thereof.

9. A composition according to any one of claims 1 to 8 wherein said polyphosphate salt comprises a pyrophosphate.

10. A composition according to claim 9 wherein said pyrophosphate comprises tetrasodium pyrophosphate.

11. A composition according to any one of claims 9 or 10 containing about 0.1 to below 3% of pyrophosphate ion.

12. A composition according to any one of claims 9 or 10 containing about 0.1 to 1.3% of pyrophosphate ion.

13. A composition according to any one of claims 1 to 12 wherein the weight ratio of polyphosphate ion:polycarboxylate salt ranges from about 0.8:1 to about 1.2:1.

14. A composition according to any one of claims 1 to 13 in the form of a toothpaste or gel further containing a dentally acceptable polishing agent and a gelling agent.

15. A composition according to any one of claims 1 to 13 in the form of a mouthwash containing an aqueous alcoholic vehicle.

16. A composition accordng to any one of claims 1 to 13 in the form of a lozenge.

17. A composition according to any one of claims 1 to 13 in the form of chewing gum.

18. A composition according to any one of claims 1 to 17 having a pH of about 4.5 to about 10.

19. A method of inhibiting dental calculus comprising applying to dental surfaces in the oral cavity a calculus-inhibiting amount of a composition as defined in any one of claims 1–18.

* * * * *